Sept. 17, 1957 C. Q. MEYERS Plant Pat. 1,640
SPIRAEA SHRUB
Filed Jan. 25, 1955
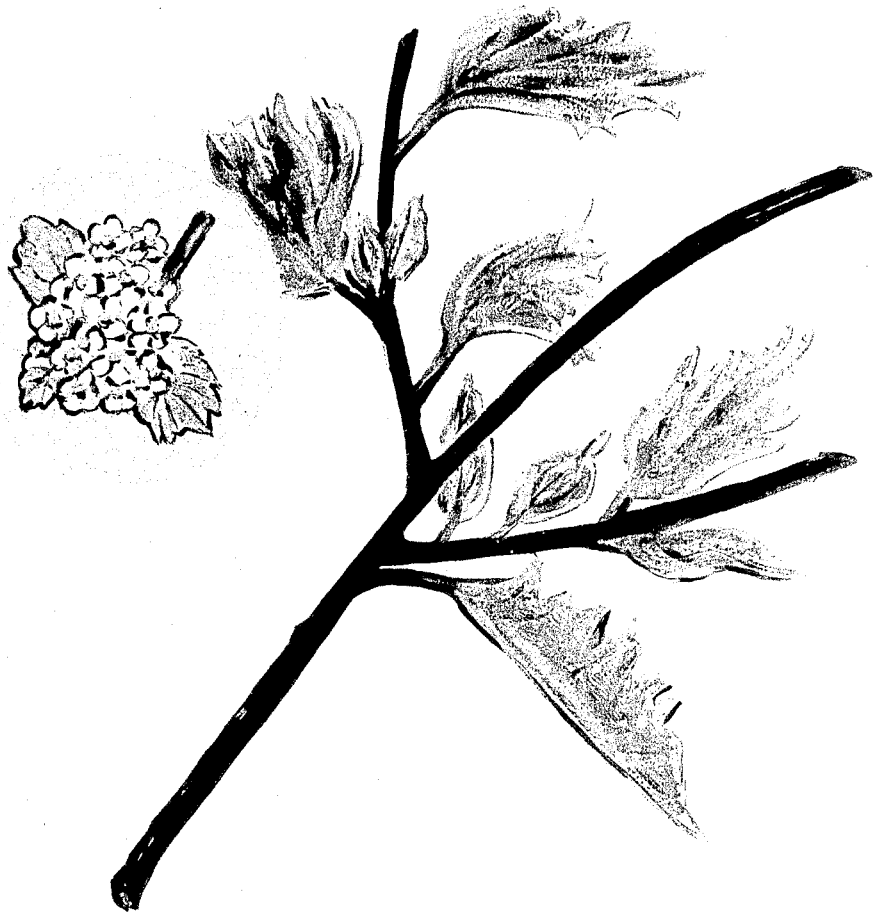
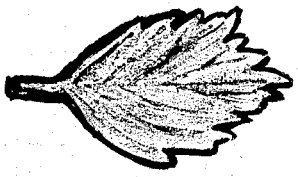
*INVENTOR.*
Charles Q. Meyers
by Talbert Dick & Adler
Attorneys United States Patent Office Plant Pat. 1,640

Patented Sept. 17, 1957

1,640

SPIRAEA SHRUB

Charles Q. Meyers, Waterloo, Iowa

Application January 25, 1955, Serial No. 484,090

1 Claim. (Cl. 47—60)

My invention relates to a new and distinct variety of spiraea shrub, the novel characteristics of which reside particularly in its dwarf habit of growth, late blooming period, upright growth, stiffness of the stems and branches, largeness and brightness of the blooms, resistance to high and low temperatures and to wet and dry conditions, and its freedom from insects and disease. The original plant of this new variety of spiraea was discovered growing in my nursery grounds near Waterloo, Iowa, in about 1932. Some five years previously I had planted five hundred (500) Spiraea Van Houtteii, unpatented, seedlings which were from one to two years old and were purchased in Faribault, Minnesota. None of these were dug for at least two years and thereafter the larger ones were dug each year as they were needed for sale with the smaller ones being left to grow. There was, of course, quite a variation in the rate of growth of the plants since they were seedlings, which would not have been the case had the plants been propagated from cuttings. By 1932 one of the plants in particular from this planting of Spiraea Van Houtteii, which was then some six or seven years old, was observed to be not only considerably smaller and slower in developing than any of the others but somewhat different in appearance. This plant was left to grow and develop and by 1934 when I moved my nursery to a new location in the same general vicinity, it had developed into a large clump which was divided into approximately twenty (20) divisions that were planted at the new location. By this time it was quite apparent that this plant was distinctly different from the parent plant and this new variety has been successfully asexually reproduced by greenwood and hardwood cuttings and from divisions to establish the characteristics shown in the accompanying drawings and more particularly identified in the following detail description.

I first asexually produced the instant plant three miles east of Waterloo, Blackhawk County, Iowa. Since that time the plant has been propagated from my stock in various localities and especially at Shenandoah, Iowa.

Presently I have growing on rich black soil some one hundred fifty (150) plants of this new variety of shrub and as yet none have been sold. Of this number, fifty (50) are at least twelve (12) years old and the other one hundred (100) are younger since they were propagated more recently. The novel characteristics of this new shrub have now been definitely established as apparent from the group of twelve (12) year old plantings and in describing them reference will be made to the characteristics of the parent shrub for comparison.

*Height.*—The twelve (12) year old shrubs have not exceeded three and one-half (3½) feet in height and in some cases are slightly shorter. In comparing this to the present Spiraea Van Houtteii which would reach a height of from six (6) to eight (8) feet in the same growing period, the dwarf habit of growth of this new variety is one of its chief novel characteristics.

*Stalks and branches.*—This shrub has a much more upright character than its parent and does not droop as much. The stalks are not as heavy and the side branches are more numerous and stiffer. The heaviest of the branches have developed to a diameter of one-half (½) inch. These characteristics are sufficiently recognizable that even dormant plants can be easily separated from the Spiraea Van Houtteii.

*Leaves.*—While the leaves bear a general similarity to the parent shrub they have certain distinct differences in that they are larger and more pointed and their edge is more serrated. All leaves on this new variety are distinctly the same so that they can be easily identified and separated from the Spiraea Van Houtteii when both are growing in the summer.

The color of the leaves is a bluish green. The color definition taken from Horticultural Colour Charts Nos. 1 and 2, by Robert F. Wilson, issued by the British Colour Council in collaboration with The Royal Horticultural Society, Printers—Henry Stone & Son (Printers Ltd., Banberry) December 1939 first volume, March 1942 second volume are as follows:

Tint—Plate 50—Block 50/3
Shade—Plate 58—Block 58/1
General tone—Plate 655—Block 655/1

*Color of bark.*—The stalks five years old and up are grey with a tinge of green. The stalks from two to five years old are a reddish brown and under two years the stalks are green. The color definition is as follows:

Stalks 5 years old and up—
Tint, Plate 824—Block 824/1
General tone, Plate 47—Block 47/3
Stalks 2 to 5 years old—
Tint, Plate 0027—Block 0027/1
General tone, Plate 00918—Block 00918/3
Stalks under and up to 2 years old—
Tint, Plate 0862—Block 0862/3
General tone, Plate 000761—Block 000761/2

*Blooms.*—These are larger than the parent variety and there are many more of them through the plants. The blooms appear two to three weeks later than Spiraea Van Houtteii and appear on the older wood of the plant as well as on the new which accounts for the heavier bloom all through the plant from the ground up. Individual florets are larger and last longer than those of the parent. The center of the floret is a greenish yellow color. The color definitions of the blooms are as follows:

Petals: Plate 645—½ intensity Block 645/3
Center of floret:
Tint, Plate 061—Block 061/2
General tone, Plate 606—Block 606/1

*Temperatures.*—Grows well in warm or hot weather and has never been frozen back. Its resistance to freezing is particularly apparent since the area where it is growing is subject to severe and extreme low temperatures in the winter.

*Dryness and wetness.*—Has never shown any deterioration either during extremely dry or wet years.

I claim:

A new and distinct variety of spiraea shrub charcterized as to novelty by its dwarf habit of growth, the lateness of its blooming period, its upright growth, the stiffness of its stems and branches which are medium brown on new growth stems and light grey on older stems and branches, the largeness and brightness of the blooms which is a brilliant white, the growth of blooms on both old and new wood throughout the plant, the leaves are a bluish green and the resistance to high and low temperatures and wet and dry conditions.

No references cited.